United States Patent [19]

Isaacson

[11] 4,207,884
[45] Jun. 17, 1980

[54] PRESSURE CONTROLLED BREATHING APPARATUS

[76] Inventor: Max Isaacson, 125 Sunrise Pl., Dayton, Ohio 45407

[21] Appl. No.: 925,173

[22] Filed: Jul. 17, 1978

Related U.S. Application Data

[63] Continuation-in-part of Ser. No. 752,183, Dec. 20, 1976, abandoned.

[51] Int. Cl.² ............................................. A61M 16/00
[52] U.S. Cl. .......................... 128/200.24; 128/204.26; 128/205.24; 128/207.16; 137/493; 251/333
[58] Field of Search ............ 128/142 R, 142.2, 142.3, 128/142.4, 142.7, 145.5, 145.6, 145.7, 145.8, 147, 2.08, 188, 202, 205, 195, 211; 137/493, 493.3, 493.8, 493.9, 524, 540, 533, 511, 543.23; 251/333

[56] References Cited

U.S. PATENT DOCUMENTS

| 731,973 | 6/1903 | Teter | 128/211 |
|---|---|---|---|
| 1,068,800 | 7/1913 | McSpirit | 128/146.5 |
| 1,162,416 | 11/1915 | Teter | 128/205 |
| 1,244,661 | 10/1917 | Teter | 128/205 |
| 2,121,311 | 6/1938 | Anderson et al. | 128/145.8 |
| 2,771,321 | 11/1956 | Alric | 251/333 X |
| 3,097,642 | 7/1963 | Russell | 128/205 X |
| 3,457,949 | 7/1969 | Coulter | 251/333 X |
| 3,881,480 | 5/1975 | Lafourcade | 128/145.6 X |
| 3,933,171 | 1/1976 | Hay | 128/188 |

FOREIGN PATENT DOCUMENTS 803000 9/1936 France ................................. 128/188

Primary Examiner—Henry J. Recla
Attorney, Agent, or Firm—Jacox & Meckstroth

[57] ABSTRACT

A medical patient or other individual exhales air through a pressure control exhalation valve at a pressure which remains substantially constant during exhalation and corresponds to the residual pressure desired within the lungs. The pressure control exhalation valve incorporates a disc-like valve member which is biased towards a closed position by a spring having a low spring modulus, and the spring engages a back-up plunger which is adjustable according to the desired residual lung pressure. The pressure control valve may be connected in series with a flow control or retard valve which is adjustable to produce a biofeedback pressure within the valve for teaching the individual to breathe slower and with less effort. During inhalation, pressurized air may be supplied to the pressure control exhalation valve through a demand inhalation valve which is adjustable to a supply pressure corresponding to the preselected exhalation pressure in order to provide for continuous positive pressure breathing.

4 Claims, 3 Drawing Figures

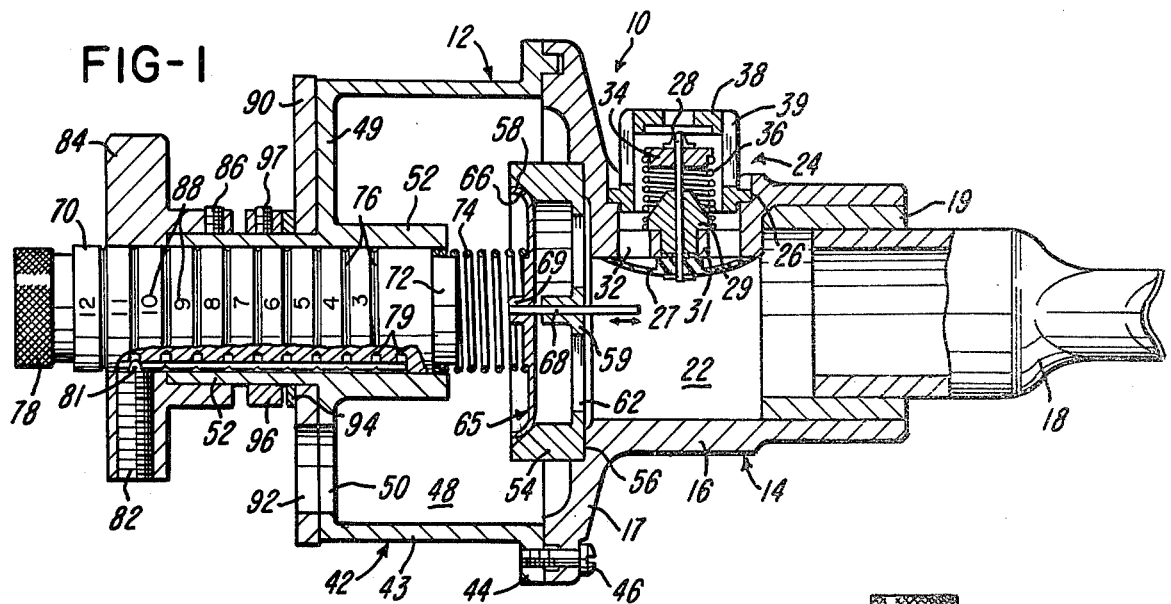
FIG-1
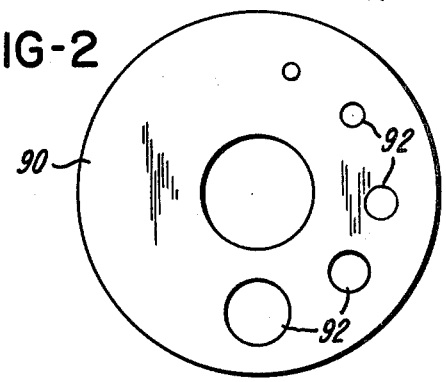
FIG-2
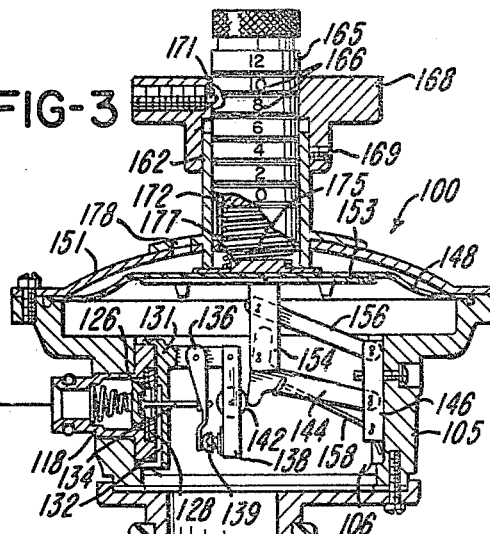
FIG-3
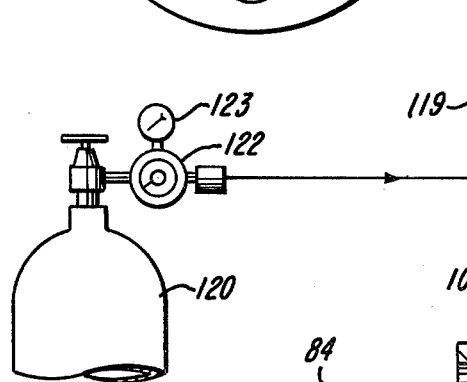
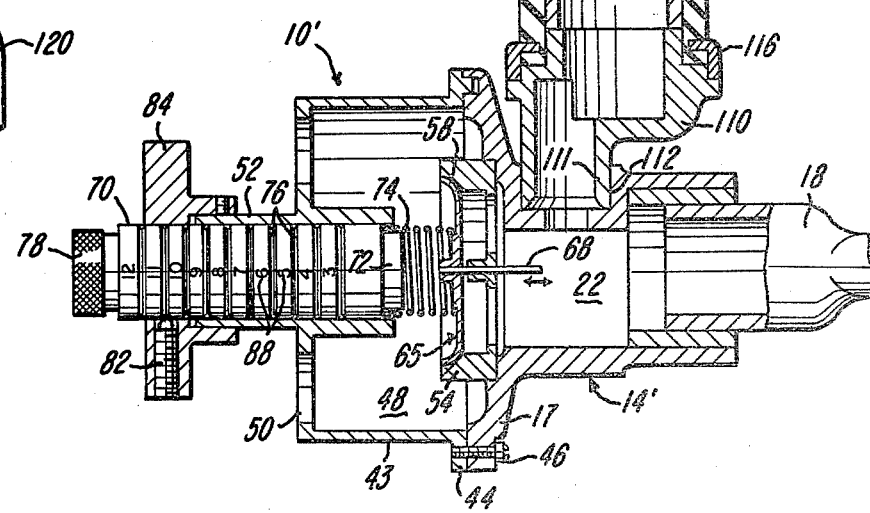

PRESSURE CONTROLLED BREATHING APPARATUS

RELATED APPLICATION

This application is a continuation-in-part of U.S. application Ser. No. 752,183, filed Dec. 20, 1976 now abandoned.

BACKGROUND OF THE INVENTION

Various types of breathing or respiratory devices have been constructed or proposed to provide pulmonary therapy to a medical patient or other individual by assisting his breathing in a manner which improves his lung capacity. Preferably, the breathing devices provide for terminating the exhalation period at a predetermined positive expiratory end or residual lung pressure, for example, between three centimeters of water and twelve centimeters of water. Such a device which provides for positive expiratory end pressure or residual lung pressure is commonly referred to as a "Peep" device.

One form of Peep device is disclosed in U.S. Pat. No. 3,710,780 wherein air is exhaled through a tube submerged within a body of water which produces a predetermined back-up pressure or head. Another form of Peep device incorporates a valve having a magnetically actuated valve member and wherein an adjustable permanent magnet controls the pressure at which the valve opens. A further type of portable Peep device resembles a smoking pipe and incorporates a spherical valve member or ball which is urged by gravity against an annular valve seat.

In view of the usual physical weakness of an individual requiring pulmonary therapy, it has been found highly desirable for a Peep device to provide for exhalation at a substantially constant predetermined Peep pressure and to offer a minimum or preselected resistance to exhalation at the Peep pressure so that minimum effort is required by the individual during exhalation. It is also important for the device to assure a positive closing or cut-off of the exhalation air flow immediately when the exhalation pressure drops below the predetermined Peep pressure to assure that the residual pressure is maintained within the lungs until at least the start of inhalation. If the device has even a small leak, the residual lung pressure quickly dissipates through the Peep device.

It has also been found desirable for the Peep device to provide for conveniently and precisely selecting between different predetermined Peep or residual lung pressures so that the device may be adjusted or regulated according to the conditions of each individual user. In addition, the device should not be dependent upon gravity for operation or require a volume of liquid so that the device may be conveniently used by an individual at any place and in any position. It is apparent after analyzing the construction and operation of the previously known Peep devices that none of the devices provide for all of the above mentioned desirable features.

SUMMARY OF THE INVENTION

The present invention is directed to an improved pressure control breathing apparatus or device which provides all of the desirable features mentioned above, particularly the exhalation of air at a substantially constant pressure corresponding to a preselected residual lung pressure and regardless of exhalation flow rate. In addition, the breathing apparatus of the invention is adapted to provide for selectively controlling the flow rate of air during exhalation by producing a bio-feedback against the pressure control exhalation valve and thus against the lungs of the patient or individual in order to train the individual to exhale at a slow rate. As another feature, the breathing apparatus of the invention provides for supplying pressurized air in response to the demand for air during inhalation and at a pressure which is selected so that it is substantially equal to or slightly below the preselected exhalation pressure whereby the breathing effort by the individual or patient is minimized and a positive pressure is maintained within the lung cells at all times.

Other features and advantages of the invention will be apparent from the following description, the accompanying drawing and the appended claims.

BRIEF DESCRIPTION OF THE DRAWING

FIG. 1 is an axial section view of a breathing or Peep device constructed in accordance with the invention for controlling exhalation;

FIG. 2 is an axial view of the flow control retard disc shown in section in FIG. 1; and FIG. 3 is an axial section of an air supply inhalation demand valve constructed in accordance with the invention and shown connected to supply air to a breathing device similar to the device shown in FIG. 1.

DESCRIPTION OF THE PREFERRED EMBODIMENTS

Referring to FIG. 1 which illustrates a device 10 constructed in accordance with the invention and used for establishing a predetermined exhalation pressure within an individual's lungs while he is exhaling, a valve body 12 is fabricated from aluminum or can be molded of a plastics material and includes a forward section 14 formed by a tubular portion 6 and an outwardly projecting flange portion 17. A tubular mouthpiece 18 connects with the tubular position 16 through a cylindrical spacer or bushing 19 and is adapted to be gripped between the lips of the individual. The valve body section 14 defines a primary inlet chamber 22, and when the individual inhales, air is drawn freely into the chamber 22 and into the lungs through a check valve 24. However, the check valve and air inlet opening may be omitted, and the individual may inhale directly through his mouth.

The check valve 24 is mounted within a stepped cylindrical recess 26 formed within the tubular portion 6 of the valve body section 14 and includes a semirigid part-spherical valve member 27 which is mounted on the inner end of a pin-like valve stem 28. The stem 28 is supported for axial sliding movement within a center bushing 29 inserted into an annular hub portion 31 supported by four spoke-like ribs 32 formed as an integral part of the body section 14. The outer end portion of the valve stem 28 carries a disc 34, and a light compression coil spring 36 engages the disc 34 for normally urging the valve member 27 to a closed position blocking the air flow through the passages defined between the ribs 32. The valve stem 28, disc 34 and spring 36 are protected by an inverted cup-shaped cover member 38 having air inlet openings defined between circumferentially spaced ribs 39.

The valve body 12 also includes a generally cylindrical rearward body section 42 which has a cylindrical wall portion 43 and an outwardly projecting forward flange portion 44 secured to the flange portion 17 by a series of peripherally spaced screws 46. The valve body section 42 defines a secondary chamber 48 and also includes a flat rear wall 49 in which is formed a relatively large diameter outlet or opening 50. The wall 49 integrally connects the cylindrical wall portion 43 with a tubular cylindrical hub portion 52 which projects both forwardly and rearwardly of the rear wall portion 49.

A cylindrical valve seat member 54 is molded of a rigid plastics material and is cemented with a counterbore 56 formed within the valve body section 14. The seat member 54 has a rearwardly facing frusto-conical valve seat 58 and includes a tubular hub portion 59 supported by radially extending spoke-like ribs 62 which define air flow passages therebetween. Preferably, the valve seat 58 has a diameter greater than one inch and on the order of 1⅛ inch. A generally flat disc-like circular valve member 64 is formed of a light weight material such as aluminum or plastic and has a peripherally extending closure surface 66 which normally engages the valve seat 58. The closure surface 66 is curved or has a radius in axial cross-sectional so that it forms a circular line contact with the frusto-conical valve seat 58. In order to maintain the closure surface 66 precisely concentric with the valve seat 58, the valve member 65 is supported by centering means including a pin-like stem 68 which is secured to the center portion 69 of the valve member 65 and is supported for axial sliding movement by the hub portion 59 of the valve seat member 54.

A generally cylindrical adjustment member or plunger 70 is supported for axial sliding movement within the hub portion 52 of the valve body section 42, and the plunger 70 has a reduced forward cylindrical end portion 72 which receives and retains one end portion of a relatively light weight coil compression spring 74. The spring 74 has a low spring rate or modulus, preferably less than 0.2 pounds per inch. One compression spring which provided desirable results had a spring rate of 0.116 pounds per inch. The forward end portion of the spring 74 engages and is retained by the center portion 69 of the valve member 65.

The adjustment plunger 70 has a series of axially spaced circumferential grooves 76 and also has a rearward end portion 78 which is adapted to be gripped with the fingers to move the plunger 70 axially within the tubular hub portion 52 of the rearward valve section 42. Each of the grooves 76 is interrupted by a small cylindrical recess 79 which successively receives a spring loaded detent ball 81 when the plunger 70 is shifted axially. The spring loaded detent ball 81 is retained by a screw 82 threaded into a radially extending hole formed within an annular collar 84. The collar 84 is adjustably secured to the rearward projecting hub portion 52 of the body section 42 by a set screw 86. The adjustment plunger 70 is calibrated with axially spaced numbers 88, corresponding to a series progressively increasing predetermined pressure increments of one centimeter of water, ranging from 3 to 12 centimeters of water illustrated. The numbers 88 are read adjacent the rearward end surface of the collar 84, for example, as the number 12 appears in the embodiment shown in FIG. 1, and each adjustment step corresponds to one centimeter of water pressure.

A circular flow control valve member or retard disc 90 is supported for rotation by the rearwardly projecting hub portion 52 of the rearward body section 42 and includes a series of circumferentially spaced flow control openings or orifices 92. The orifices 92 vary in diameter, for example, between 7/64 inch and 7/16 inch and may be selectively positioned in alignment with the outlet opening 50. The flow control disc 90 is pressed against the rearward surface of the wall 46 by an annular wavy-type spring 94 for frictionally retaining the disc. The spring 94 surrounds the hub portion 52 and is retained by a cylindrical collar 96 secured to the hub portion 52 by a set screw 97.

In operation of the exhalation control apparatus or device illustrated in FIG. 1, the patient or individual requiring pulmonary therapy inhales through the mouthpiece 18, as mentioned above. During inhalation, air flows freely inwardly through the check valve 24 since a light suction shifts the valve member 27 inwardly to open the passages for the inflow of air. The plunger 70 is adjusted axially to indicate the desired Peep or residual lung pressure, for example, ranging from 3 to 12 centimeters of water. When the individual exhales through the mouthpiece 18, the disc-like valve member 65 shifts rearwardly by a slight distance to an open position as soon as the exhalation pressure within the chamber 22 reaches the pressure corresponding to the predetermined pressure selected by adjustment of the plunger 70.

Because of the generally flat configuration of the valve member 65, a high drag force is produced on this valve member during exhalation, and this drag force makes the valve member more responsive to pressure changes than if this valve member were streamlined or spherical. In addition, the large diameter of the valve seat 58 and valve member 65 provide for a large annular passage defined between the valve seat 58 and the closure surface 66 of the valve member 65 so that a relatively small axial movement of the valve member 65, such as 1/16 inch, against the bias of the spring 74 significantly increases the area of the annular flow passage defined between the seat 58 and surface 66. The low spring rate or modulus of the back-up or closing spring 74 further provides for moving the valve member further from the seat 58 with only an extremely slight increase in exhalation pressure. All these effects combine to limit the maximum exhalation pressure within the chamber 22 below the next successively higher pressure increment above the exhalation pressure selected with the plunger 70 and independent of the exhalation flow rate. Thus if the individual commences to exhale at a rate higher than his normal exhalation flow rate, the annular flow passage through the valve immediately increases by a substantial percentage so that the exhalation pressure does not significantly increase above the desired Peep pressure as determined by the setting of the plunger 70. When the exhalation pressure decreases slightly to the preselected Peep pressure, the valve member 65 immediately closes so that the residual pressure within the individual's lungs is held at the preselected Peep pressure until the beginning of inhalation.

By proper use of the flow retard member 90, the user of the device can be taught to exhale with minimum effort. This is accomplished by first exhaling with the retard plate 90 in a position such that the largest orifice 92 is positioned over the opening 50. This arrangement produces the minimum exhalation resistance. After feeling this minimum exhalation resistance (bio-feedback), the user is instructed to set the retard plate at the next smaller opening and to exhale slowly so that the exhalation resistance feels approximately the same as when the larger orifice was used. This step can be repeated with successively smaller orifices 92 to teach the user to exhale as slowly as possible in attempting to achieve the same resistance feel to exhalation with the small orifice as with the largest orifice. Thus a simple comparision of the exhalation resistance of one opening relative to another will indicate to him by bio-feedback the proper exhalation techniques. The slower exhalation is desired in order to maintain the air pressure within the lungs for as long as possible so that the lung cells are exposed to oxygen for as long as possible during each period of exhalation.

Referring to FIG. 3, the exhalation device 10 shown in FIG. 1 is also adapted to be used in combination with an inhalation control device 100 in order to provide for positive pressure breathing during both inhalation and exhalation. Thus the combination provides for a positive pressure within the individual's lungs at all times and also minimizes the effort required for breathing. In the embodiment of FIG. 3, the exhalation control device 10' is constructed the same as the device shown in FIG. 1 with the exception that the flow control or retard valve member 90 has been omitted, and the inhalation check valve 24 is replaced by the inhalation control device 100. Thus the same reference numbers are used in FIG. 3 to identify the common components or structure.

In general, the inhalation control device 100 is constructed to operate in the same manner as the demand valve or inhalator disclosed in U.S. Pat. No. 2,989,970. The inhalation control device 100 includes a valve body 105 which defines an internal chamber 106 and has a tubular outlet portion 108. The tubular output portion 108 is connected to the body section 14' of the exhalation control device 10' by an adaptor 110 which is molded of a rigid plastics material and has a tubular portion 111 cemented within an inlet opening 112 formed within the body section 14'. A resilient tubular sleeve 114 receives the outlet portion 108 of the valve body 105 and is couples to the adaptor 110 by a retaining ring 116 and cement.

Pressurized air is supplied to the valve chamber 106 through a tubular inlet fitting 118 connected by a flexible hose or line 119 to a source or pressurized air or oxygen. As illustrated in FIG. 3, a tank 120 of compressed air is connected to the line 119 through an adjustable regulator 122 which is connected to a pressure indicating gauge 123. The regulator valve 122 is adjusted to provide a predetermined air supply pressure within the line 119, for example, 50 PSI.

The inlet fitting 118 encloses a spring-biased valve member 126 which normally closes a center opening within a washer-like valve seat member 128. The valve seat member 128 is retained by a bracket 131 which defines a passage 132 for directing the air from the fitting 118 into the valve chamber 106. A valve actuating stem 134 extends through a hole within the bracket 131 and has an outer end which engages the valve member 126. The inner end of the valve stem 134 is coupled to a lever 136 pivotally supported by an inwardly projecting arm of the bracket 131. A second actuating lever 138 is also pivotally supported by the bracket arm, and an adjustable screw 139 is secured to the lower end of the lever 138 and has a head which engages the lower end portion of the lever 136. The lever 138 carries a roller 142 which engages the inner cam surface on the head of an arm 144 pivotally supported by a bracket 146 secured to the inner surface of the valve body 105. If desired, a nebulizer may be connected into the passage 132 in order to aspirate a liquid medication into the inflow of air downstream of the valve member 126.

A flexible circular diaphragm 148 has an outer peripheral portion secured to the valve body 105 by an outwardly projecting flange portion of a cover plate 151. The flexible diaphragm 148 overlies a rigid metal diaphragm plate 153, and a bracket 154 depends from the diaphragm plate 153 and is pivotally connected to the inner head portion of the arm 144. The bracket 154 is also pivotally connected to the inner end portion of a link element 156, and the outer end portion of the link element 156 is also pivotally connected to the bracket 146. The link element 156 cooperates with the arm 144 to form a generally parallelogram linkage system to produce generally linear movement of the diaphragm plate 153. A wire spring 158 extends between the bracket 146 and the arm 144 and normally urges the arm 144 upwardly to release the force exerted on the actuating stem 134 so that the valve member 126 remains normally closed.

A tubular support hub 162 is secured to the center portion of the cover member 151 and slidably supports an axially adjustable plunger 165 which is constructed substantially the same as the plunger 70 described above in connection with FIG. 1. Thus the plunger 165 is calibrated with numbers 166 which preferably also correspond to pressures in centimeters of water. The numbers are read or viewed adjacent the outer end surface of an annular collar 168 adjustably mounted on the tubular hub member 162 by a set screw 169. The collar 168 retains a spring-loaded detent ball 171 which is adapted to engage a series of axially spaced recesses 172 formed within the plunger 165. The inner end portion of the plunger 165 retains one end of a compression coil spring 175 which also has a low spring rate or modulus similar to that of the spring 74. The inner end portion of the spring 175 is retained by a plate 177 secured to the center portions of the flexible diaphragm 148 and the supporting diaphragm plate 153. A hole 178 in the cover member 151 provides for atmospheric pressure above the diaphragm 148.

In the operation of the positive pressure breathing device shown in FIG. 3, when the individual inhales through the mouthpiece 18, the flexible diaphragm 148 and the diaphragm plate 153 senses the predetermined inhalation pressure and move downwardly. The arm 144 pivots the levers 136 and 138 in a clockwise direction to shift the valve stem 134 and the valve member 126 from the valve seat member 128, thereby opening the inlet valve so that the pressurized air within line 119 flows through the chamber 106 and into the mouthpiece 18. The plunger 165 is adjusted so that air is supplied through the inhalator device 100 at a pressure slightly below the desired exhalation pressure as determined by the setting of the plunger 70 of the exhalation control device 10'. For example, the inhalation control device 100 may be set to supply air on demand at 8 centimeters of water at the beginning of inhalation, and the exhalation control device 10' may be set to close at 10 centimeters of water at the end of exhalation. As soon as the individual begins to exhale through the mouthpiece 18, the demand inhalator valve device 100 closes.

It is thus apparent that the combined inhalation and exhalation devices shown in FIG. 3 provide for minimizing the pressure differential between inhalation and exhalation so that minimum effort is required by the individual for breathing. Thus the device may be used by extremely weak people, for example, for pulmonary therapy soon after surgery. The combined devices shown in FIG. 3 also provide for maintaining a positive above atmospheric pressure within the individual's lungs both during inhalation and during exhalation so that the alveoli or air cells within the lungs remain full of air at all times. Furthermore, the pressures for inhalation and exhalation can be conveniently adjusted simply by adjusting the corresponding inhalation control plunger 165 and the exhalation control plunger 70.

As mentioned above, the exhalation control device shown in FIG. 1 is particularly designed for maintaining a substantially constant pressure within the lungs during exhalation by maintaining the pressure differential between the maximum exhalation pressure and the opening exhalation pressure below one increment of calibrated pressure on the plunger 70. Thus the exhalation effort by the individual does not significantly increase above the effort required to open the valve member 65 at the predetermined Peep pressure. As a result of the large diameter of the annular valve seat 58 and the closure surface 66, which is preferably greater than one inch, only a small axial movement of the valve member 65 provides an annular flow passage of substantial area. Thus if the individual attempts to exhale quickly, the pressure within the chamber 22 is not significantly increased above the pressure at which the valve member 65 opens. For example, during an exhalation rate of 500 c.c. within one second, the maximum pressure increase within the inlet chamber 22 remains less than a pressure increment of one cm of water above the preset Peep pressure at which the valve member 65 opens.

It is also important that the effective area of the generally flat valve member 65, exposed to exhalation pressure, should be such that the drag effect on the valve member upon exhalation does not materially cause the exhalation pressure to exceed the preset pressure acting on the valve member by the biasing means or spring 74. Furthermore, the axial adjustment of the plunger 70 also provides for precisely selecting the expiratory end or residual Peep pressure which is best suited for the condition of the lungs of the individual. In addition, the rotatably adjustable flow retard control disc 90 provides a means for training the individual to exhale at a slower rate by creating a feedback pressure within the chamber 48 tending to urge the valve member 65 towards its closed position, thereby restricting the exhalation flow rate of the individual.

As mentioned above, the curved closure surface 66 of the disc-like valve member 65 cooperates with the frusto-conical seat 58 and the centering means 59 and 68 to assure that the valve member 65 closes immediately when the pressure in the inlet chamber 22 drops below the selected Peep pressure, and regardless of the position or orientation of the breathing device. It is also within the scope of the invention to provide a pressure responsive signal device, such as a whistle, to sense the pressure at the outlet 50 and to indicate to the user that his exhalation rate is too high.

While forms of breathing apparatus herein described constitute preferred embodiments of the invention, it is to be understood that the invention is not limited to these precise forms of apparatus and that changes may be made therein without departing from the scope and spirit of the invention as defined in the appended claims.

The invention having thus been described, the following is claimed:

1. In apparatus for controlling an individual's exhalation and including a body defining a chamber having an inlet and an outlet, means for directing the individual's exhalation into said inlet, an exhalation pressure responsive control valve within said chamber for controlling the flow of exhalation gas through said inlet and outlet to atmosphere, said valve including an annular valve seat and a generally flat valve member, means supporting said valve member for axial movement between a closed position engaging said valve seat and an open position spaced from said valve seat, a compression coil spring biasing said valve member towards said closed position, and means for adjusting the axial force exerted by said spring against said valve member, the improvement for adapting said apparatus to be used in pulmonary therapy, wherein said coil spring has a spring rate less than 0.2 pound per inch, said adjusting means for said spring include a series of uniformally spaced indicators corresponding to a series of progressively increasing uniform pressure increments and providing for selecting a predetermined exhalation pressure corresponding to the opening pressure at which said valve member moves from said valve seat to an open position, wherein said adjusting means having said pressure increments, the spring, the valve member and the valve seat are designed such that during an exhalation phase, for each said pressure increment selected, the valve member will move from the valve seat to said open position a distance causing sufficient annular area between the valve member and valve seat that the differential force against the valve member caused by exhalation flow required to move the valve member said distance is smaller than the differential force that would be exerted on the valve member by said spring if said adjusting means would be adjusted from said selected pressure increment to the next higher pressure increment, whereby said spring and valve member cooperate to limit the maximum exhalation pressure within said chamber below the next successively higher pressure increment to said selected pressure increment of said adjusting means and for maintaining the pressure differential between the maximum pressure and the opening pressure below the pressure differential of said pressure increments during the individual's exhalation and substantially independent of the individual's exhalation flow rate.

2. Apparatus as defined in claim 1 in combination with a demand valve connected to said valve body for supplying air upstream of said exhalation pressure control valve member and in response to inhalation, means for adjusting the air supply pressure within said chamber, and said adjusting means including a series of uniformally spaced indicators corresponding to said indicators for selecting the individuals exhalation pressure.

3. Apparatus as defined in claim 1 wherein said adjusting means comprise an axially movable plunger having a plurality of axially spaced recesses corresponding to the different exhalation pressures, and detent means for successively engaging said recesses to retain said plunger at a preselected exhalation pressure.

4. In apparatus for controlling an individual's exhalation and including a body defining a chamber having an inlet and an outlet, means for directing the individual's exhalation into said inlet, an exhalation pressure responsive control valve within said chamber for controlling the flow of exhalation gas through said inlet and outlet to atmosphere, said valve including an annular valve seat and a generally flat valve member, means supporting said valve member for axial movement between a closed position engaging said valve seat and an open position spaced from said valve seat, a compression coil spring biasing said valve member towards said closed position, and means for adjusting the axial force exerted by said spring against said valve member, the improvement for adapting said apparatus to be used in pulmonary therapy, wherein said coil spring has a spring rate less than 0.2 pound per inch, said adjusting means for said spring include an axially movable plunger having a series of uniformly axially spaced indicators corresponding to a series of progressively increasing uniform pressure increments and providing for selecting a predetermined exhalation pressure corresponding to the opening pressure at which said valve member moves from said valve seat to an open position, spring detent means for retaining said plunger at each of said indicators, wherein said plunger having said pressure increments, the spring, the valve member and the valve seat are designed such that during an exhalation phase, for each said pressure increment selected, the valve member will move from the valve seat to said open position a distance causing sufficient annular area between the valve member and valve seat that the differential force against the valve member caused by exhalation flow required to move the valve member said distance is smaller than the differential force that would be exerted on the valve member by said spring if said plunger would be adjusted from said selected pressure increment to the next higher pressure increment, whereby said spring and valve member cooperate to limit the maximum exhalation pressure within said chamber below the next successively higher pressure increment to said selected pressure increment of said adjusting means and for maintaining the pressure differential between the maximum pressure and the opening pressure below the pressure differential of said pressure increments during the individual's exhalation and substantially independent of the individual's exhalation flow rate.

* * * * *